US006706781B2

(12) United States Patent
Rajaiah et al.

(10) Patent No.: US 6,706,781 B2
(45) Date of Patent: Mar. 16, 2004

(54) DENTURE ADHESIVE COMPOSITIONS WITH ANTIMICROBIAL AGENTS

(75) Inventors: Jayanth Rajaiah, Loveland, OH (US); Kimberly Ann Gilday-Weber, Cincinnati, OH (US); Lisa Catron Ernst, Cincinnati, OH (US); Thinh Nguyen Ha, Cincinnati, OH (US); John E. Barnes, Maineville, OH (US); Nivedita Ramji, Mason, OH (US); Ann Maria Kneipp, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/218,651

(22) Filed: Aug. 14, 2002

(65) Prior Publication Data

US 2003/0108489 A1 Jun. 12, 2003

Related U.S. Application Data

(63) Continuation-in-part of application No. 09/716,766, filed on Nov. 20, 2000, now Pat. No. 6,475,497, said application No. 60/169,703, filed on Dec. 8, 1999, and application No. 60/169,558, filed on Dec. 8, 1999, which is a continuation-in-part of application No. 09/716,810, filed on Nov. 20, 2000, now Pat. No. 6,677,391.

(60) Provisional application No. 60/169,702, filed on Dec. 8, 1999.

(51) Int. Cl.$^7$ .............................. A61K 6/00; A61K 7/22
(52) U.S. Cl. ....................................... 523/120; 424/54
(58) Field of Search ............................ 523/120; 424/54

(56) References Cited

U.S. PATENT DOCUMENTS

| 3,534,887 A | * | 10/1970 | Ginsberg .................... 222/107 |
| 3,956,480 A | | 5/1976 | Dichter et al. |
| 4,415,551 A | | 11/1983 | Fang |
| 5,055,046 A | * | 10/1991 | Chaudhuri et al. .......... 523/120 |
| 5,066,709 A | * | 11/1991 | Chaudhuri et al. .......... 524/516 |
| 5,525,330 A | | 6/1996 | Gaffar et al. |
| 5,575,652 A | * | 11/1996 | Gaffar et al. ................ 433/173 |
| 5,700,478 A | * | 12/1997 | Biegajski et al. ............ 424/434 |
| 5,800,832 A | * | 9/1998 | Tapolsky et al. ............ 424/449 |
| 5,955,097 A | * | 9/1999 | Tapolsky et al. ............ 424/434 |
| 6,103,266 A | * | 8/2000 | Tapolsky et al. ............ 424/484 |
| 6,124,374 A | * | 9/2000 | Kolias et al. ................ 523/120 |
| 6,159,498 A | * | 12/2000 | Tapolsky et al. ............ 424/449 |
| 6,290,984 B1 | * | 9/2001 | Tapolsky et al. ............ 424/436 |
| 6,315,987 B1 | | 11/2001 | Plochocka |
| 6,375,963 B1 | * | 4/2002 | Repka et al. ................ 424/402 |
| 6,432,415 B1 | * | 8/2002 | Osborne et al. ............. 424/400 |

FOREIGN PATENT DOCUMENTS

| DE | 20014749 | 8/2000 |
| JP | 11049625 | 2/1999 |
| JP | 11221238 | 8/1999 |
| WO | WO 01/41710 | 6/2001 |
| WO | WO 01/41711 | 6/2001 |

OTHER PUBLICATIONS

Procter & Gamble Patent application s/n 09/537,348, filed Mar. 29, 2000.
Procter & Gamble Patent application s/n 09/537,380, U.S. patent 6,355,706.
Procter & Gamble Patent application s/n 09/291,554, filed Apr. 19, 1999.
Procter & Gamble Patent application s/n 09/389,209, filed Sep. 2, 1999.

* cited by examiner

*Primary Examiner*—Shep K. Rose
(74) *Attorney, Agent, or Firm*—Betty J. Zea

(57) ABSTRACT

The present invention relates to methods and compositions for reducing, inhibiting, and/or preventing, calculus, tartar, plaque, and/or microbes, in the oral cavity, comprising from about 15% to about 70% of an alkyl vinyl ether maleic copolymer or terpolymer denture adhesive component, an effective amount of a quaternary ammonium antimicrobial agent selected from the group consisting of cetylpyridinium chloride, domiphen bromide, and mixtures thereof, and a non-aqueous vehicle. A denture wearer in need thereof applies the composition to the oral cavity and/or the denture prosthesis and thereafter secures the denture to the oral cavity.

13 Claims, No Drawings

DENTURE ADHESIVE COMPOSITIONS WITH ANTIMICROBIAL AGENTS

This aplication is a continuation-in-part of U.S. Ser. No. 09/716,766, filed Nov. 20, 2000 now U.S. Pat. No. 6,475,497, which claims the benefit of Ser. No. 60/169,703, filed Dec. 8, 1999; U.S. Ser. No. 09/716,820, filed Nov. 20, 2000 now U.S. Pat. No. 6,475,498, which claims the benefit of Ser. No. 60/169,558 filed Dec. 8, 1999 and U.S. Ser. No. 09/716,810, filed Nov. 20, 2000 now U.S. Pat. No. 6,677,391, which claims the benefit of Ser. No. 60/169,702 filed Dec. 8, 1999.

TECHNICAL FIELD

The present invention relates to compositions and methods for reducing, inhibiting, and/or preventing, calculus, tartar, plaque, and/or microbes, in the oral cavity, by applying a non-aqueous denture adhesive composition comprising an alkyl vinyl ether maleic copolymer or terpolymer denture adhesive component, a quaternary ammonium antimicrobial agent selected from the group consisting of cetylpyridinium chloride, domiphen bromide, and mixtures thereof, and a non-aqueous vehicle. These compositions provide the above benefits, while providing superior and sustained denture hold.

BACKGROUND OF THE INVENTION

Ordinary removable dentures, dental plates and the like, comprise teeth mounted in a suitable plate or base. Denture stabilizers are used to fill the interstices between the dentures and the gums or tissues. Prior to placement of the denture in the oral cavity, a denture stabilizer is applied to the denture-plate surface which, for a perfect fit, should uniformly contact the gums and mucous tissues. The denture stabilizer is formulated not only for its adherent properties, but also to provide a cushion or gasket between the denture and the gums or tissues, thereby positioning the denture securely in the oral cavity.

Considerable effort has been made over the years to develop improved denture adhesive compositions. Both synthetic and natural polymers and gums have been used alone, in combination, and in combination with various other adhesive materials in an attempt to improve hold and reduce oozing of the adhesive from under the dental plate. These compositions also enhanced the removal of the residual adhesive from the mouth and dentures. For example, alkyl vinyl ether-maleic copolymers and salts thereof are known for providing good hold in denture adhesive compositions. Such disclosures include: U.S. Pat. No. 3,003,988, Germann et al., issued Oct. 10, 1961; U.S. Pat. No. 4,980,391, Kumar et al., issued Dec. 25, 1990; U.S. Pat. No. 5,073,604, Holeva et al., issued Dec. 17, 1991; U.S. Pat. No. 5,525,652, Clarke, issued Jun. 11, 1996; U.S. Pat. No. 5,340,918, Kittrell et al., issued Aug. 23, 1994; U.S. Pat. No. 5,830,933, Synodis et al., issued Nov. 3, 1998.

In addition strip/wafer type denture adhesives are also known. For example, U.S. Pat. No. 4,880,702 to Homan et al., issued Nov. 14, 1989 discloses a denture stabilizer in the form of a strip consisting of three layers. EP 353,375, Altwirth, published Feb. 7, 1990, discloses an adhesive insert for dentures consisting of a adhesive permeated fibrous fleece and an adhesive consisting of a pasty mixture of alginate and/or carboxymethylcellulose, polyvinyl acetate and an alcoholic solvent.

Cationic germicides are also known in the art. See, for instance *Quaternary Ammonium and Related Compounds—Antiseptics and Disinfectants*, Kirk-Othmer Encyclopedia of Chemical Technology, 2nd Ed. (Vol. 2 p. 632–635), incorporated herein by reference.

The combination of anionic polymers and cationic germicides has been generally disclosed in the art for application directly to the teeth (see for example U.S. Pat. No. 3,956,480, Dichter et al., issued May 11, 1976). This prior art, however, is generally restricted to the use of aqueous dispersions thereof or to the use of low levels of the anionic polymer, these low levels being well below the levels generally used for denture adhesive compositions. Not only is the release parameters of the cationic germicide unpredictable in denture adhesive compositions in light of the high levels of AVE/MA polymers utilized, denture adhesive compositions additionally comprise non-aqueous carriers, generally comprising hydrocarbons, which can further interact with the release and/or activity of the cationic germicide in the denture adhesive composition.

Despite the above-noted technologies as well as others, a need still exists for denture stabilizing compositions providing both improved and sustained hold as well as antimicrobial, antitartar, antiplaque, and anticalculus benefits in the oral cavity of the denture wearer. The present invention relates to compositions and methods for reducing, inhibiting, and/or preventing, calculus, tartar, plaque, and/or microbes, in the oral cavity, by applying a non-aqueous denture adhesive composition comprising an alkyl vinyl ether maleic copolymer and/or terpolymer denture adhesive component, an effective amount of a quaternary ammonium antimicrobial agent selected from the group consisting of cetylpyridinium chloride, domiphen bromide, and mixtures thereof, and a non-aqueous vehicle. These compositions provide the above benefits, while providing superior and sustained denture hold.

SUMMARY OF THE INVENTION

The present invention relates to compositions for reducing, inhibiting, and/or preventing, calculus, tartar, plaque, and/or microbes, in the oral cavity, comprising from about 15% to about 70% of an alkyl vinyl ether maleic copolymer and/or terpolymer denture adhesive component, an effective amount of a quaternary ammonium antimicrobial agent selected from the group consisting of cetylpyridinium chloride, domiphen bromide, and mixtures thereof, and a non-aqueous vehicle, in one embodiment the non-aqueous vehicle comprises a hydrocarbon material.

In addition the present invention relates to denture adhesive compositions comprising the above composition and at least one non-adhesive self-supporting layer. The present invention further relates to a method for reducing, inhibiting, and/or preventing, calculus, tartar, plaque, and/or microbes, in the oral cavity, by applying the above composition to the oral cavity of a denture wearing subject in need thereof and thereafter securing the denture to the ridge or palate of the oral cavity.

DETAILED DESCRIPTION OF THE INVENTION

A detailed description of essential and optional components of the present invention is given below.

Definitions

The term "safe and effective adhesive amounts" or "effective adhesive amount", as used herein, means an amount sufficient to provide adherence to the oral cavity and/or adherence of a dental prosthesis to the palate and/or ridge of the oral cavity, without toxicity to the user, damage to oral tissue, and alteration of the denture material.

By "safe and effective amount", as used herein, is meant an amount of an agent (e.g., antimicrobial agent) high enough to significantly (positively) modify the condition to be treated, but low enough to avoid serious side effects (at a reasonable benefit/risk ratio), within the scope of sound medical/dental judgment. The safe and effective amount of an agent may vary with the particular condition being treated, the age and physical condition of the patient being treated, the severity of the condition, the duration of treatment, the nature of concurrent therapy, the specific form of the source employed, and the particular vehicle from which the agent is applied.

The term "AVE/MA" as used herein refers to alkyl vinyl ether-maleic acid or anhydride copolymer. The term "AVE/MA/IB" refers to terpolymers with alkyl vinyl ether, maleic acid or anhydride, and isobutylene. The term "mixed polymer salts" or "mixed salts", as used herein, refers to salts of AVE/MA and/or AVE/MA/IB where at least 2 different cations are mixed on the same polymer with each other or with other ester functions.

The term "free acid" "FA" component, as used herein, refers either to the unreacted carboxyl groups (—COOH) of AVE/MA copolymer and/or AVE/MA/IB plus any other monovalent cations of carboxyl groups; e.g., —COONa, of the polymer. Monovalent cations include Group IA cations, such as sodium, potassium, hydrogen, etc. Preferably, the term "free acid" refers to the unreacted carboxyl groups (—COOH) of AVE/MA and/or AVE/MA/IB plus sodium and potassium cations. More preferably, the term "free acid" refers only to the unreacted carboxyl groups (—COOH) of the AVE/MA and/or AVE/MA/IB.

The term "additional adhesive component", as used herein, refers to adhesives other than those described as essential AVE/MA and/or AVE/MA/IB salts of the present invention.

The percentages used herein to describe the salts function of the copolymers or terpolymer are defined as the stoichiometric percent of the total initial carboxyl groups reacted on the polymer.

All other percentages used herein are by weight unless otherwise indicated. All references cited herein are herein incorporated by reference in their entirety.

Denture Adhesive Component

The present invention comprises a safe and effective adhesive amount of a denture adhesive component, generally at a level of from about 15% to about 70%, in another embodiment from about 20% to about 50%, and in another embodiment from about 25% to about 50%, by weight of the composition. In one embodiment the compositions of the present invention comprise at least 20 percent by weight, and in another embodiment at least 30 percent by weight of the composition, of a denture adhesive component.

The denture adhesive component is selected from the group consisting of AVE/MA, salts of AVE/MA, AVE/MA/IB, salts of AVE/MA/IB, and mixtures thereof.

The alkyl vinyl ether-maleic acid copolymer comprises the repeated structural unit:

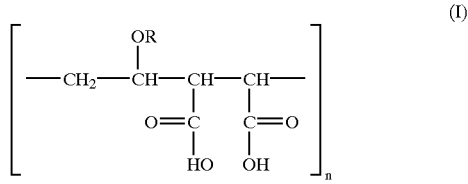

(I)

wherein R represents an alkyl radical, preferably a $C_1$ to $C_5$ alkyl radical, n is an integer greater than one representing the number of repeated occurrences of the structural unit in a molecule of the polymer.

The "terpolymer" or "terpolymer with isobutylene" means a terpolymer of maleic anhydride or acid, an alkyl vinyl ether (in one embodiment with a $C_1$–$C_5$ alkyl radical), and isobutylene, having a structure of $(A-B)_n$ where A is maleic anhydride or acid and B is alkyl vinyl ether (preferably with a $C_1$–$C_5$ alkyl radical), and/or isobutylene. The specific viscosity of the starting anhydride or acid of the terpolymer is preferably at least about 5.5, preferably at least about 6, preferably measured as a 1% weight/volume solution of methyl ethyl ketone at 25° C. The terpolymer must contain at least some isobutylene.

In one embodiment, the adhesive component is AVE/MA and salts thereof, preferably mixed salts of AVE/MA, wherein the copolymer contains a cationic salt function comprising a cation selected from the group consisting of Group IA and Group 2A cations of the periodic table, yttrium, titanium, zirconium, vanadium, chromium, manganese, iron, nickel, copper, zinc, boron, aluminum, cations and mixtures thereof. In another embodiment, the adhesive component is a mixed salt of AVE/MA containing a cationic salt function comprising a cation selected from the group consisting of strontium, zinc, iron, boron, aluminum, vanadium, chromium, manganese, nickel, copper, yttrium, titanium, magnesium, calcium, sodium, cations and mixtures thereof, and in yet another embodiment the the cation is selected from the group consisting of strontium, zinc, iron, magnesium, calcium, sodium, cations, and mixtures thereof.

AVE/MA contains, in one embodiment, a cationic salt function comprising from about 5% to about 50%, in another embodiment, from about 10% to about 40%, in yet another embodiment, from about 10% to about 35% (of the total initial carboxyl groups reacted) zinc cations. These zinc cations can be mixed with other cations selected from the group consisting of: from about 1% to about 65%, preferably from about 10% to about 60%, calcium and/or magnesium cations, from about 0.001% to about 2.5%, preferably from about 0.01% to about 2% of iron, boron, aluminum, vanadium, chromium, manganese, nickel, copper, yttrium, and/or titanium cations, and mixtures thereof.

The present denture adhesive compositions comprise mixed salts of an AVE/MA copolymer and/or terpolymer wherein the mixed salt contains a cationic salt function comprising (or in the alternative consists essentially of) an effective adhesive amount of, in another embodiment from about 5% to about 50% zinc cations and/or calcium cations and from 0% to about 10% of a cation selected from the group consisting of strontium, magnesium, sodium, iron, boron, aluminum, vanadium, chromium, manganese, nickel, copper, yttrium, titanium, and mixtures thereof, of the total initial carboxyl groups reacted, the mixed salt containing from about 30% to about 60% free acid component.

The AVE/MA copolymers have a range of specific viscosities. For example, the specific viscosity is preferably from 1.2 to 14, as preferably measured as a 1% weight/volume solution of the starting anhydride or acid of the copolymer, in methyl ethyl ketone at 25° C. Other methods and solvents can be used to measure the specific viscosity such as a 1% weight/volume solution in DMF (dimethyl formamide) at 25° C. and a 1% weight/volume solution in 2-butanone at 25° C.

In one embodiment the the cation is selected from the group consisting of strontium, zinc, iron, magnesium, calcium, sodium, cations, and mixtures thereof, at a total level of each cation from about 0.1% to about 60%, more preferably from about 5% to about 55%, of the initial carboxyl groups reacted. In addition, preferably the cationic salt function contains from about 10% to about 45% zinc, more preferably from about 15% to about 40% zinc cations, of the initial carboxyl groups reacted; preferably from about 0.001% to about 2.5%, more preferably from about 0.01% to about 2% of a cation selected from the group consisting of iron, boron, aluminum, vanadium, chromium, manganese, nickel, copper, yttrium, titanium, and mixtures thereof, more preferably from about 0.01% to about 2% iron cations, of the initial carboxyl groups reacted. Preferably the cationic salt function contains from about 37.5% to about 55%, more preferably from about 37.5% to about 50%, free acid component, of the total initial carboxyl groups.

AVE/MA and salts thereof and AVE/MA/IB and salts thereof, are also described in U.S. Pat. No. 5,073,604 to Holeva et al., issued Nov. 17, 1991; U.S. Pat. No. 5,525,652, issued Jun. 11, 1996, Clarke et al.; U.S. Pat. No. 4,758,630, issued Jul. 19, 1988, Shah et al.; U.S. Pat. No. 5,304, 616, issued Apr. 19, 1994, Rajaiah et al.; U.S. Pat. No. 5,424,058, issued Jun. 13, 1995, Rajaiah; 5,424,058, issued Jun. 13, 1995, Rajaiah et al.; U.S. Pat. No. 4,758,630, issued Jul. 19, 1988, Shah et al.; U.S. Pat. No. 5,830,933, issued Nov. 3, 1998, Synodis et al.; U.S. Pat. No. 2,047,398, issued Jul. 14, 1936, Voss et al.; U.S. Pat. No. 3,003,988, issued Oct. 10, 1961, Germann et al.; U.S. Pat. No. 5,880,172, Rajaiah et al., issued Mar. 9, 1999; U.S. Pat. No. 5,900,470, Prosise et al., issued May 4, 1999; U.S. Pat. No. 5,037,924, Tazi et al., issued Aug. 6, 1991; U.S. Pat. No. 5,082,913, Tazi et al, issued Jan. 21, 1992; U.S. Pat. No. 6,239,191, issued May 29, 2001; all of which are incorporated herein by reference in their entirety.

In one embodiment the free acid level of the salts of the AVE/MA or AVE/MA/IB is at least about 36%, in another embodiment is from about 36% to about 60%, and even in another embodiment is from about 40% to about 55%, of the total initial carboxyl groups of the copolymer or terpolymer.

Suitable AVE/MA copolymers may be prepared by well-known methods of the prior art; see, for example, U.S. Pat. No. 2,782,182, and U.S. Pat. No. 2,047,398, both of which are incorporated by reference herein in their entirety. The terpolymers can be made by the methods discussed in U.S. Pat. No. 5,900,470, Prosise et al., issued May 4, 1999; U.S. Pat. No. 5,037,924, Tazi et al., issued Aug. 6, 1991; and U.S. Pat. No. 5,082,913, Tazi et al., issued Jan. 21, 1992, herein incorporated by reference in their entirety.

The alkyl vinyl ether maleic anhydride copolymers are obtained by co-polymerizing an alkyl vinyl ether monomer, such as methyl vinyl ether, ethyl vinyl ether, divinyl ether, propyl vinyl ether and isobutyl vinyl ether, with maleic anhydride to yield the corresponding alkyl vinyl ether-maleic anhydride copolymer which is readily hydrolyzable to the acid copolymer. Both anhydride and acid forms are also available from commercial suppliers. For example, the ISP Corporation, Wayne, N.J. provides both the polymeric free acid form (I) and the corresponding anhydride form under its "GANTREZ" trademark as the "GANTREZ S Series" and "GANTREZ AN Series", respectively. When the anhydride copolymer dissolves in water, the anhydride linkage is cleaved so that the highly polar, polymeric free acid (I) is formed. Accordingly, the anhydride form, which is relatively less expensive than the acid form, may be used as a convenient and cheaper precursor for the acid. Elevated temperatures may be advantageously employed to enhance the rate of anhydride-to-acid hydrolysis.

The salt form of the subject polymers may be prepared by the interaction of the AVE/M anhydride or acid copolymer or terpolymer with at least one cationic salt function, such as magnesium, zinc, calcium, sodium, potassium, iron, or ammonium compounds having a functional group typical of reactants of a carboxylic acid, such as, for example, the hydroxide, oxide, acetate, halide, lactate, etc. in an aqueous medium. In a preferred embodiment, the zinc oxide, magnesium oxide, combined with strontium carbonate and/or calcium hydroxide are utilized. Mixed polymer salts comprising iron cations can be prepared by the interaction of the AVE/M anhydride/acid polymers with iron compounds, in the form of a salt, such as iron sulfate n-hydrate.

Ions that form toxic, irritating or contaminating by-products should be avoided, or special precautions and treatment provided to assure the removal and absence of such by-products from the polymeric salt end-product. The particular compound used should be substantially pure to assure obtaining a substantially pure, polymeric salt end-product.

For example, if the salt form of the polymer is desired, then an aqueous dispersion of particulate zinc oxide is combined with magnesium oxide (or combined with strontium carbonate and/or calcium hydroxide) and, optionally, ferric sulfate n-hydrate. This is combined with the powder polymer, in the form of a slurry, in an amount sufficient to provide the desire cationic content desired in the end-product. This is done at ambient temperature and then slowly heated to 70°–95° C. with continuous vigorous mixing so as to prevent localized precipitation of the cationic polymeric salt; mixing is continued to ensure that all the salt forming compound is reacted with the copolymer.

Alternatively, the polymer is hydrolyzed and neutralized in an aqueous mixture or slurry of one or more divalent and/or monovalent metal bases by heating the copolymer/base mixture to a temperature ranging from about 45° C to about 100° C. Reaction of the mixed polymer salt with iron cations is obtained through addition of iron salts to the hydrolyzed and neutralized mixed salt of the polymer. Completion of the reaction with iron cations is indicated by an increase in viscosity to stabilization. Alternatively, iron salts may be blended with the polymer/metal base mixture prior to the hydrolysis and neutralization reactions.

In either of the above processes, the resulting slurry or solution is transferred to shallow stainless steel drying trays and placed in a forced air mechanical convection oven at 60–70° C. for a time sufficient to evaporate the reaction medium (water) and remove water from the polymer (about 18–24 hours). Alternatively, the resulting slurry or solution can be drum-dried at 100° to 200° C. with hot steam to evaporate the water content and recover the polymer in the flake form. After drying, the polymer forms brittle flakes which can easily be peeled off from the trays or drum surface and ground to a fine powder as desired to provide satisfactory denture stabilizing properties. Methods of making these mixed salts of AVE/MA polymers are further disclosed in U.S. Pat. Nos. 5,073,604, Holeva et al., issued Dec. 17, 1991; 5,872,161, Liang et al., issued Feb. 16, 1999; 5,830, 933, Synodis et al., issued Nov. 3, 1998, all of which are herein incorporated by reference in their entirety.

The mixed salt polymers have exceptional adhesive qualities when contacted with water or saliva such that they are extremely useful as denture adhesive materials in denture compositions.

The Antimicrobial Agent

The present compositions comprise a safe and effective amount of an antimicrobial agent selected from the group consisting of cetylpyridium chloride, domiphen bromide, and mixtures thereof. The level of antimicrobial agent is generally from about 0.00001% to about 10% by weight of the composition, in another embodiment is from about 0.001% to about 8%, in yet another embodiment is from about 0.01% to about 5%, in yet another embodiment is from about 0.09% to about 1%, and in yet another embodiment is from about 0.1% to about 0.5%, by weight of the composition. Despite the presence of high levels of negatively charged AVE/MA or AVEIMA/IB polymers in the composition, an effective amount of the antimicrobial agent is released from the denture adhesive composition to provide anticalculus, antiplaque, antitartar and/or antimicrobial efficacy. Also this release is achieved despite the presence of non-aqueous vehicles generally comprising linear hydrocarbon materials which can also interact with the linear hydrocarbon portion of the antimicrobial agent. In addition the release of an effective amount of the the antimicrobial agent from the composition, once release begins, is sustained for at least about 1 hour, in another embodiment for at least about 4 hours, in another embodiment from about 2 hours to about 4 hours, in yet another embodiment from about 4 hours to about 6 hours, and in yet another embodiment from about 6 hours to about 8 hours or longer. The antimicrobial agent should also be essentially compatible with the other components of the composition.

Non-Aqueous Denture Adhesive Carrier

The non-aqueous denture adhesive carrier is selected from the group consisting of a non-aqueous vehicle and a non-adhesive self supporting layer. The level of non-aqueous vehicle is from about 10% to about 90%, in another embodiment is from about 15% to about 80%, in yet another embodiment is from about 20% to about 60%, and in yet another embodiment is from about 30% to about 55%, by weight of the composition.

Non-aqueous Vehicles

The non-aqueous vehicle is generally any chemical in any physical form that does not contain water. In one embodiment the non-aqueous vehicle is selected from the group consisting of saturated or non-saturated hydrocarbons or derivatives thereof, liquid petrolatum, petrolatum, mineral oil, natural and synthetic oils, fats, natural and synthetic waxes such as animal waxes like beeswax, lanolin and shellac, vegetable oil waxes such as carnauba, candelilla and bayberry wax, vegetable oils, and mixtures thereof. In another embodiment the non-aqueous vehicle is selected from the group consisting of liquid petrolatum, petrolatum, mineral oil, vegetable oils such as corn, soy bean, cottonseed, castor, palm and coconut oils and animal oil such as fish oil, and mixtures thereof; and in yet another embodiment is liquid petrolatum, petrolatum, mineral oil, and mixtures thereof.

Non-Adhesive Self-Supporting Layer

The non-aqueous carrier can comprise at least one non-adhesive self-supporting layer. The non-adhesive self-supporting layer is characterized by its ability to maintain strength and provide integrity for the adhesive composition in the presence of water and/or saliva. The non-adhesive self-supporting layer may include materials such as polyester, polypropylene, nylon, rayon, cellulose acetate, non-adhesive cellulose derivatives, cloth, fibrous fleece, paper, plastic, leather, microcrystalline wax, synthetic fibers, natural fibers, and mixtures thereof. Preferred are non-adhesive cellulose derivatives, polyester, polypropylene, nylon, rayon, cloth, paper, microcrystalline wax, and mixtures thereof. More preferred are polyester, polypropylene, rayon, nylon, cloth and paper.

The non-adhesive self-supporting layer may be in any physical form suitable for providing strength and/or integrity to the present adhesive compositions. Such physical forms include non-woven, woven, continuous, chopped, foam, and combinations thereof. In addition, the non-adhesive self-supporting layer may be formed by any process commonly known in the art. Such processes include un-bonded, spraybonded, spun-bonded, needle-punched, carded, thermal bonded hydroentangled, meltblown, aperture print bonded, needled, wet-laid, dry-laid, and combinations thereof.

The present denture adhesive compositions which comprise a non-adhesive self-supporting layer may also comprise a coating which is sticky to dry dentures and, if present, will be placed on one side of the denture adhesive composition. Compositions suitable for use as this type of adhesive layer include silicones, rubbers, petrolatum, natural polymers, synthetic polymers, and mixtures thereof. The adhesive layer may be present at a level of from about 0% to about 70%, and in another embodiment from about 0.5% to about 20%, by weight of the composition.

Optional Ingredients

Other Adhesive Components

The present compositions may also include other adhesive components. These adhesive components, if present, are used in a safe and effective adhesive amounts. In general, the other adhesive components may be present at a level of from about 0% to about 90%, in one embodiment from about 10% to about 70%, and in another embodiment from about 20% to about 50%, by weight of the composition.

Suitable adhesive components may include a water-soluble hydrophilic colloid or polymer having the property of swelling upon exposure to moisture to form a mucilaginous mass. In one embodiment the other adhesive components are selected from the group consisting of: natural gums, synthetic polymeric gums, AVE/MA acid, AVE/MA anhydride, AVE/MA/IB acid, AVE/MA/IB anhydride, synthetic polymers, mucoadhesive polymers, hydrophilic polymers, saccharide derivatives, cellulose derivatives, and mixtures thereof. In another embodiment the other adhesive components are selected from the group consisting of: natural gums, synthetic polymeric gums, AVE/MA acid, AVE/MA anhydride, AVE/MA/IB acid, AVE/MA/IB anhydride, cellulose derivatives, and mixtures thereof. Examples of such materials include karaya gum, guar gum, gelatin, algin, sodium alginate, tragacanth, chitosan, polyethylene glycol, acrylamide polymers, cross-linked polyacrylic acid, polyvinyl alcohol, polyamines, polyquarternary compounds, polybutenes, silicones, ethylene oxide polymers, polyvinylpyrrolidone, cationic polyacrylamide polymers, and mixtures thereof.

In one embodiment these other adhesives are selected from the group consisting of cellulose derivatives, polyethylene glycol, polyethylene oxide, karaya gum, sodium alginate, chitosan, polyvinyl alcohol, and mixtures thereof. In one embodiment these other adhesives are selected from the group consisting of cellulose derivatives such as methylcellulose, carboxymethylcellulose, hydroxyethylcellulose, hydroxypropylcellulose, hydroxypropylmethylcellulose, and mixtures thereof.

Plasticizers

In addition one or more toxicologically-acceptable plasticizers may also be included in the present compositions. The term "toxicologically-acceptable", as used herein, is used to describe materials that are suitable in their toxicity profile for administration to humans and/or lower animals. Plasticizers that may be used in the present compositions include dimethyl phthalate, diethyl phthalate, dioctyl phthalate, glycerin, diethylene glycol, triethylene glycol, sorbitol, tricresyl phosphate, dimethyl sebacate, ethyl glycolate, ethylphthalyl ethyl glycolate, o- and p-toluene ethyl sulfonamide, and mixtures thereof. Plasticizers may be present at a level of from about 0% to about 50%, preferably from about 1% to about 30%, by weight of the compositions.

Flavors, Fragrance, Sensates

The compositions of the present invention may also include one or more components which provide flavor, fragrance, and/or sensate benefit (warming or cooling agents). Suitable components include natural or artificial sweetening agents, menthol, menthyl lactate, wintergreen oil, peppermint oil, spearmint oil, leaf alcohol, clove bud oil, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof, as well as coolants.

The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979; the disclosure of both are herein incorporated by reference in their entirety. These agents may be present at a level of from about 0% to about 50%, by weight of the composition.

Other Active Ingredients

The present adhesive compositions can be used to deliver one or more therapeutic actives suitable for topical administration to mucosal or wet tissues. The phrase "therapeutic actives", as used herein, describes agents which are pharmacologically active when absorbed through wet tissue or mucosal surfaces of the body such as the oral cavity. Therapeutic actives may be present at a level of from about 0% to about 50%, by weight of the composition.

Therapeutic actives that are useful in the present compositions include anti-inflammatory agents such as aspirin, acetaminophen, naproxen and its salts, ibuprofen, ketorolac, flurbiprofen, indomethacin, eugenol, or hydrocortisone; dentinal desensitizing agents such as potassium nitrate, strontium chloride or sodium fluoride; anesthetic agents such as lidocaine or benzocaine; anti-fungals; aromatics such as camphor, eucalyptus oil, aldehyde derivatives such as benzaldehyde; insulin; and steroids. It is recognized that in certain forms of therapy, combinations of these agents in a single delivery system may be useful in order to obtain an optimal effect.

Other Optional Ingredients

Other suitable ingredients include colorants, preservatives such as methyl and propyl parabens; and thickeners such as silicon dixode and polyethylene glycol. Colorants, preservatives, and thickeners may be present at levels of from about 0% to about 20%, preferably from about 2% to about 10%, by weight of the composition.

Process for Preparation of the Composition

A process for preparing denture adhesive compositions of the present invention (creams, powders, wafers, liquids, aerosols, pastes) comprises conventional methods disclosed in the art. Conventional methods are taught in U.S. Pat. No. 5,525,652, issued Jun. 11, 1996, Clarke et al.; U.S. Pat. No. 3,003,988, issued Oct. 10, 1961, Germann et al.; U.S. Pat. No. 5,073,604, Holeva et al., issued Dec. 17, 1991; and U.S. Pat. No. 5,872,161, Liang et al., issued Feb. 16, 1999, all of which are herein incorporated by reference in their entirety.

A process for the preparation of the present denture adhesive compositions optionally comprising a non-adhesive self-supporting layer, comprises coating a weighed amount of the adhesive components onto the non-adhesive self-supporting layer. This process is disclosed in U.S. Pat. No. 5,877,233, Liang et al, issued Mar. 2, 1999; U.S. Pat. No. 5,872,160, issued Feb. 16, 1999, Liang et al.; U.S. Pat. No. 5,880,172, Rajaiah et al., filed Oct. 25, 1996, all of which are incorporated herein by reference in their entirety.

Composition Use

The present invention also relates to method for reducing, inhibiting, and/or preventing, calculus, tartar, plaque, and/or microbes, in the oral cavity, by applying, to the oral cavity of a denture wearing subject in need thereof, a composition comprising from about 15% to about 70% of an alkyl vinyl ether maleic copolymer or terpolymer denture adhesive component, an effective amount of a quaternary ammonium antimicrobial agent selected from the group consisting of cetylpyridinium chloride, domiphen bromide, and mixtures thereof, and a non-aqueous vehicle, in one embodiment the non-aqueous vehicle comprises a hydrocarbon material. The adhesive compositions may be in the form of a powder, cream, paste, liquid, aerosol, and/or wafer. The subject in need thereof applies (either by spraying or otherwise) the above composition, in any form, to the dentures of a denture wearer in need thereof, and/or to the oral cavity, and/or to the palate or ridge of the oral cavity, and thereafter secures the denture to the ridge or palate of the oral cavity.

Powder forms are sprinkled on a dental prosthesis, moistened and then inserted into the oral cavity. Denture adhesive compositions with a self-supporting layer are thoroughly moistened, then applied to dentures, and thereafter inserted into the oral cavity.

EXAMPLES

The following examples further describe and demonstrate embodiments within the scope of the present invention. The examples are given solely for the purpose of illustration and are not to be construed as limitations of the present invention. Many variations of these are possible without departing from the spirit and scope of the invention.

Example I

Denture stabilizing compositions in cream form can be made by blending together the following ingredients:

|  | A Gram | B Grams | C Grams | D Grams | E Grams | F Grams | G Grams |
| --- | --- | --- | --- | --- | --- | --- | --- |
| Salt or mixed salt of AVE/MA or AVE/MA/IB[1] | 33 | 33 | 33 | 33 | 33 | 33 | 33 |
| Carboxymethylcellulose | 20 | 20 | 20 | 20 | 20 | 20 | 20 |
| Mineral Oil | 23.95 | 23.95 | 23.95 | 23.95 | 23.95 | 23.95 | 23.95 |
| Petrolatum | 21.9 | 21.9 | 21.9 | 21.9 | 21.81 | 20.91 | 11.01 |
| CPC | 0.0000 | 0.0001 | 0.001 | 0.01 | 0.1 | 1 | 10 |
| Silica | 1.14 | 1.14 | 1.14 | 1.14 | 1.14 | 1.14 | 1.14 |

[1]The salt cation is selected from the group consisting of calcium, zinc, magnesium, strontium, sodium, iron, and mixtures thereof.

Weigh, heat and mix the petrolatum and mineral oil in a glass jar at 50° to 60° C. until visually uniform. Then weigh and shake-blend the powders (silica CMC, AVE/MA copolymer salt) together in a container. Thereafter, mix the powders into the liquid with a spatula until visually a uniform cream. The above cream composition can also be modified by using mixtures of the various AVE/MA mixed polymer salts.

A denture wearer places from about 0.1 grams to 5 grams of any of the compositions described above on the denture. Then the subject inserts the denture into the mouth and presses it into place. After applying this composition, the composition minimizes, inhibits, tartar, calculus, plaque and/or microbed, and/or kills microbes in the oral cavity.

Example II

Denture stabilizing compositions in powder form can be made by blending together the following ingredients:

|  | weight (grams) |
| --- | --- |
| CPC | 0.1 |
| Carboxymethylcellulose Sodium | 40.00 |
| Any salt or mixed salt of AVE/MA[2] | 60.00 |

Blend all components together. The above compositions can be modified by increasing or decreasing the CPC by 0.05 to 0.5 grams. The above powder compositions can also be modified by using mixtures of the various AVE/MA mixed salts. The subject places from 0.1 to 2 grams of the composition on a pre-moistened denture, allowing it to hydrate briefly. Then the subject inserts the denture into his/her mouth and presses it into place. After applying the composition, the composition minimizes, inhibits tartar, plaque, calculus, and/or microbes, in the oral cavity.

Example III

|  | A Grams | B Grams | C Grams | D Grams | E Grams | F Grams | G Grams |
| --- | --- | --- | --- | --- | --- | --- | --- |
| Ca/ZN, Mg/ZN/Na, and/or Mg/ZN salt of AVE/MA | 30 | 30 | 30 | 30 | 30 | 30 | 30 |
| Acid form of AVE/MA | 0 | 0.1 | 1 | 2 | 5 | 1 | 1 |
| Carboxymethylcellulose | 24 | 24 | 24 | 24 | 24 | 24 | 24 |
| Mineral Oil | 23.95 | 23.95 | 23.95 | 23.95 | 23.95 | 23.95 | 23.95 |
| Petrolatum | 20.81 | 20.71 | 19.81 | 18.81 | 15.81 | 19.9 | 18.91 |
| CPC | 0.1 | 0.1 | 0.1 | 0.1 | 0.1 | 0.01 | 1 |
| Silica | 1.14 | 1.14 | 1.14 | 1.14 | 1.14 | 1.14 | 1.14 |

[2]The salt is selected from the group consisting of zinc, calcium, strontium, iron, magnesium, sodium, and mixtures thereof.

Weigh, heat and mix the petrolatum and mineral oil in a glass jar at 50° to 60° C. until visually uniform. Then weigh and shake-blend the powders (silica CMC, AVE/MA acid and copolymer salt) together in a container. Thereafter, mix the powders into the liquid with a spatula until visually a uniform cream. The above cream composition can also be modified by using mixtures of the various AVE/MA mixed polymer salts. A denture wearer places from about 0.1 grams to 5 grams of any of the compositions described above on the denture. Then the subject inserts the denture into the mouth and presses it into place. After applying this composition, the composition minimizes, inhibits, tartar, plaque, calculus and/or microbes in the oral cavity.

Example IV

Denture stabilizing compositions in wafer form can be made by wetting a 58" by 20" non-woven polyester (non-adhesive self-supporting layer) with water. Uniformly coat this wet sheet with the compositions listed below. Thereafter, rewet the layer with water. Dry the layer. Mechanically soften the composition by ring-roller, and then smooth the composition on a hydraulic press. Die-cut the composition into desired shapes. Moisten and apply these wafer compositions to the dentures. Then the subject inserts the denture into the mouth and presses it into place. After applying this composition, the composition minimizes, inhibits, tartar, plaque, calculus and/or microbes in the oral cavity.

|  | weight (grams) |
|---|---|
| CPC | 0.2 |
| Carboxymethylcellulose Sodium | 60.00 |
| Ca/ZN, Mg/ZN/Na, and/or Mg/ZN salt of AVE/MA | 90.00 |

What is claimed is:

1. A denture adhesive composition comprising;
   (a) from about 30% to about 70% of a denture adhesive component selected from the group consisting of salts of AVE/MA, salts of AVE/MA/IB, and mixtures thereof;
   (b) from about 0.00001% to about 8% by weight of the composition of an antimicrobial agent selected from the group consisting of cetyl pyridium chloride, domiphen bromide, and mixtures thereof; and
   (c) from about 10% to about 90% by weight of the composition of a non-aqueous denture adhesive carrier;
   wherein the salt contains a cationic salt function comprising a cation selected from the group consisting of Group IA and Group 2A cations of the periodic table, yttrium, titanium, zirconium, vanadium, chromium, manganese, nickel, copper, zinc, boron, aluminum, sodium, strontium, zinc, iron, magnesium, calcium, sodium, and mixtures thereof.

2. The composition of claim 1 wherein the level of antimicrobial agent is from about 0.001% to about 3%, by weight of the composition.

3. The composition of claim 2 wherein the level of antimicrobial agent is from about 0.09% to about 1%, by weight of the composition.

4. The composition of claim 3 wherein the level of antimicrobial agent is from about 0.1% to about 0.5%, by weight of the composition.

5. The composition of claim 1 wherein the non-aqueous denture adhesive carrier is selected from the group consisting of a non-aqueous vehicle and a non-adhesive self supporting layer.

6. The composition of claim 5 wherein the non-aqueous carrier is a non-aqueous vehicle selected from the group consisting of liquid petrolatum, petrolatum, mineral oil, natural and synthetic oils, fats, natural and synthetic waxes, vegetable oil waxes, vegetable oils, and mixtures thereof.

7. The composition of claim 6 wherein the non-aqueous vehicle is selected from the group consisting of liquid petrolatum, petrolatum, mineral oil, and mixtures thereof.

8. The composition of claim 5 wherein the non-aqueous carrier is a non-adhesive self-supporting layer.

9. The composition of claim 8 wherein the non-adhesive self-supporting layer is selected from the group consisting of polyester, polypropylene, nylon, rayon, cellulose acetate, non-adhesive cellulose derivatives, cloth, fibrous fleece, paper, plastic, leather, synthetic fibers, natural fibers, and mixtures thereof.

10. A method of delivering an antimicrobial agent to the oral cavity and teeth of a denture wearer in need thereof, by applying the composition of claim 1 to a denture prosthesis, the oral cavity, or both, and thereafter securing the denture prosthesis to the oral cavity.

11. A method of reducing, inhibiting, or preventing calculus, plaque, tartar or microbes in the oral cavity, of a denture wearer in need thereof, by applying the composition of claim 1 to a denture prosthesis, the oral cavity, or both, and thereafter securing the denture prosthesis to the oral cavity.

12. The composition of claim 1 further comprising an additional adhesive component selected from the group consisting of natural gums, hydrophilic polymers, cellulose derivatives, AVE/MA copolymer acid, and mixtures thereof.

13. The composition of claim 12 wherein the additional adhesive component is a cellulose derivative selected from the group consisting of hydroxyethylcellulose, hydroxypropylcellulose, hydroxypropylmethyl-cellulose, sodium carboxymethylcellulose, and mixtures thereof.

* * * * *